United States Patent [19]
Silver et al.

[11] Patent Number: 5,641,322
[45] Date of Patent: Jun. 24, 1997

[54] ORTHOPEDIC KNEE BRACE SUSPENSION SYSTEM WHICH INCLUDES NON-SLIPPAGE INFLATABLE AIR PILLOWS AND A PUMP

[75] Inventors: Daniel M. Silver, Los Angeles; Russell A. Rothenberg, Santa Monica, both of Calif.

[73] Assignee: S. R. Orthopedic Laboratories Inc., Santa Monica, Calif.

[21] Appl. No.: 609,919

[22] Filed: Feb. 29, 1996

Related U.S. Application Data

[63] Continuation of Ser. No. 368,023, Jan. 3, 1995, abandoned.
[51] Int. Cl.[6] ........................................ A61F 5/00
[52] U.S. Cl. ..................... 602/13; 602/26; 128/DIG. 20
[58] Field of Search .................................. 602/5, 13, 16, 602/26, 23; 128/DIG. 20; 417/432

[56] References Cited

U.S. PATENT DOCUMENTS

| | | | |
|---|---|---|---|
| 4,702,235 | 10/1987 | Hong | 602/13 |
| 5,107,823 | 4/1992 | Fratesi | 602/26 X |
| 5,152,302 | 10/1992 | Fareed | 602/13 X |
| 5,230,695 | 7/1993 | Silver et al. | 602/13 |
| 5,310,400 | 5/1994 | Rogers et al. | 602/13 X |
| 5,437,615 | 8/1995 | Pekar et al. | 602/13 X |
| 5,450,858 | 9/1995 | Zablotsky et al. | 602/13 X |

*Primary Examiner*—Linda C. Dvorak

[57] ABSTRACT

An orthopedic knee brace which includes a pump, the orthopedic knee brace also including a thigh cuff and a pair of inflatable air pillows interposed between the thigh cuff and the thigh of the wearer to prevent slippage. The pillows are mounted on the thigh cuff in positions located on the opposite side of the femur of the wearer within the medial femoral hollows in position to engage the femoral condyles. The pump is mounted on the thigh cuff, and it serves to inflate and deflate the air pillows. The pump includes a hollow housing, together with a release valve mounted at an accessible position on the housing to permit the air pillows to be conveniently deflated when desired.

2 Claims, 1 Drawing Sheet

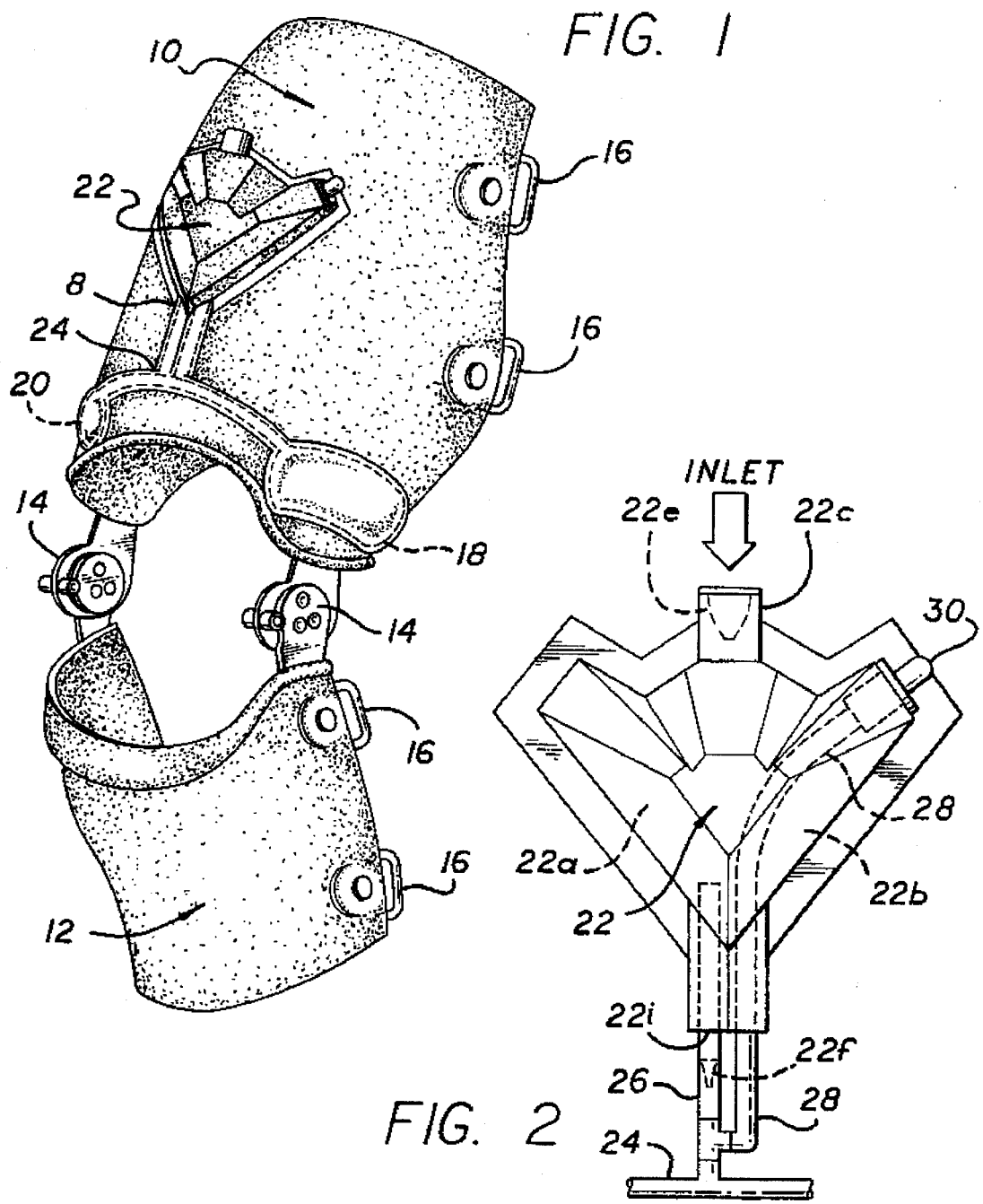
FIG. 1
FIG. 2
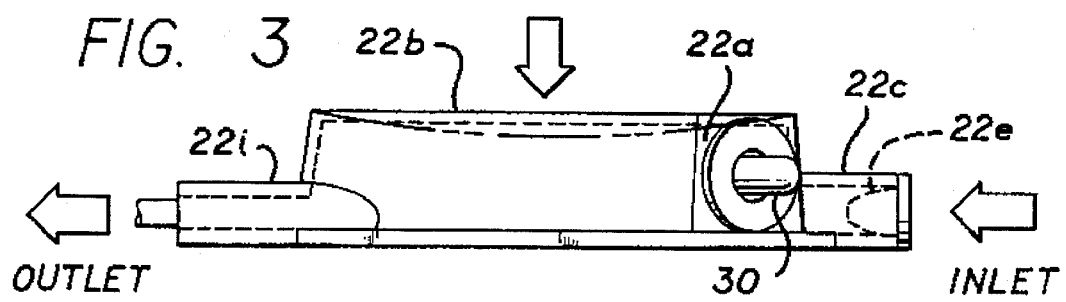
FIG. 3

ORTHOPEDIC KNEE BRACE SUSPENSION SYSTEM WHICH INCLUDES NON-SLIPPAGE INFLATABLE AIR PILLOWS AND A PUMP

BACKGROUND OF THE INVENTION

This application is a continuation of application Ser. No. 08/368,023 filed Jan. 3, 1995, now abandoned in the names of the present inventors.

The invention relates generally to an improved orthopedic knee brace suspension system which includes air pillows and a manually operated pump for inflating the air pillows, for an orthopedic knee brace of the type disclosed in U.S. Pat. No. 5,230,695 which issued Jul. 27, 1993. The orthopedic knee brace disclosed in the patent is constructed to control ligament instability, and it includes upper and lower cuffs joined together by specially-designed polycentric hinges of the type described, for example, in U.S. Pat. No. 5,230,696 which issued Jul. 27, 1993; and in co-pending application Ser. No. 08/368,021 filed Jan. 3, 1995.

A typical knee brace of the general type disclosed in U.S. Pat. No. 5,230,695 is described, for example, in U.S. Pat. No. 4,966,133—Kausek. As pointed out in that patent, when the ligament surrounding the knee has been traumatized by injury or by surgery, a supporting brace is commonly used to provide stability to the knee while still permitting movement of the knee. The brace must provide stability when forces are applied to the knee in the medial or lateral (side) planes, and in the anterior (frond and posterior (rear) planes. In addition, the brace must provide rotational stability to prevent excessive axial rotation of the tibia with respect to the femur. the brace must also prevent forward movement of the tibia with respect to the femur, a function provided in the normal knee by the anterior creciate ligament.

As pointed out in U.S. Pat. No. 5,230,695, a problem encountered in the prior art knee braces is the tendency, particularly for the upper cuff which surrounds the thigh of the wearer, to slip down along the thigh. The upper cuff is normally held in place by straps with Velcro fasteners, and in view of the slippage tendency, it is often difficult to adjust the straps for optimum stability and comfort because of the tendency for the upper cuff to slip down along the thigh of the patient due to muscle action.

The orthopedic brace disclosed in U.S. Pat. No. 5,230,695 includes a simple means which is easily adjustable to assure that the upper (thigh) cuff may be mounted for optimum effect and comfort and still be held firmly in place without excessive slippage despite muscle action of the wearer. The foregoing is achieved in the brace of U.S. Pat. No. 5,230,695 by mounting one or more air pillows between the thigh of the wearer and the cuff, and by providing a miniature manually operated pump coupled to the air pillows. The pump permits the wearer to pump the air pillows to a desired inflated condition to hold the cuff firmly in place without affecting the comfort of the wearer.

An objective of the present invention is to provide an improved orthopedic knee brace suspension system which includes air pillows and which also includes a manually operated pump for inflating the air pillows. The improved knee brace suspension system of the invention may be generally similar to the knee brace described in U.S. Pat. No. 5,230,695; the knee brace of the present invention being constructed also to incorporate an easily accessible manually operated release valve for enabling the air pillows to be deflated when so desired.

BRIEF DESCRIPTION OF THE DRAWINGS

FIG. 1 is a perspective representation of the upper and lower cuffs and interconnecting hinges of an orthopedic knee brace similar to the knee brace disclosed in U.S. Pat. No. 5,230,695, and which includes a pump constructed in accordance with the concepts of the present invention for inflating air pillows included in the brace;

FIG. 2 is a top plan view of the pump of the invention which is mounted on the upper cuff of the knee brace of FIG. 1 for inflating the air pillows; and FIG. 3 is a side elevational view of the pump of FIG. 2.

DETAILED DESCRIPTION OF THE ILLUSTRATED EMBODIMENT

As stated above, FIG. 1 is a perspective representation of a portion of an orthopedic knee brace which includes an upper cuff 10 which engages the thigh of the wearer, and a lower cuff 12 which engages the leg of the wearer below the knee. The upper and lower cuffs 10 and 12 are hinged to one another by appropriate hinges 14. The upper and lower cuffs are formed, for example, of a Kevlar/fiberglass composition, or any other appropriate material. The cuffs are conventionally held in place by straps connected to the cuffs through fastener brackets 16, with the straps surrounding the thigh and leg of the wearer, being held in place by appropriate fasteners such as Velcro fasteners.

As described in U.S. Pat. No. 5,230,695, a pair of air pillows 18 and 20 are interposed between the upper cuff 10 and the thigh of the wearer. The air pillows are positioned to be located on opposite sides of the femur of the wearer within the lateral and medial femoral hollows in the distal femoral metaphysis area of the femur. The air pillows 18 and 20 engage the femoral condyles so that when the air pillows are inflated, they firmly hold the upper brace 10 from slipping, since any downward slippage is prevented by the engagement of the air pillows with the condyles.

The air pillows 18 and 20 are inflated by a miniature air pump 22 constructed in accordance with the invention, and which is shown in detail in FIGS. 2 and 3. The air pump 22 permits the wearer, by repeatedly depressing and releasing the resilient top of the pump, to introduce pressurized air into the air pillows through a tube 24.

It will be appreciated that the knee brace shown in FIG. 1 may be easily mounted on the leg of the wearer, with the upper and lower cuffs 10 and 12 being held in place by appropriate straps (not shown). Then, the pump 22 is operated to inflate the air pillows 18 and 20, thereby causing the air pillows to hold the upper cuff 10, and other components, from slipping down the thigh of the wearer. The inflated air pillows firmly and positively hold the upper cuff and associated components in place around the thigh of the wearer because of their engagement with the condyles of the patient's femur, thereby preventing any slippage of the upper cuff, this being achieved without detracting in any way from the comfort of the device.

The miniature pump 22, as shown in FIGS. 2 and 3, may be formed of an integral resilient plastic material to define a housing 22a having a resilient top 22b. The pump has a generally triangular configuration, as shown in FIGS. 1 and 2, with an inlet 22c open to the atmosphere formed at one end, and an outlet 22i formed at the other end and coupled to an outlet tube 26. A resilient "duck bill" valve 22e is inserted into the inlet 22c, and a second resilient "duck bill" valve 22f is inserted into the outlet 22i. The "duck bill" valves are positioned so that when the resilient top 22b is depressed, any air within the housing 22a is expelled into the air bladders (pillows) 18 and 20 at relatively high pressure through the outlet 22i and through tubes 26 and 24. Then, when the resilient top 22b is released, air is drawn into the housing 22a through the inlet 22c. Accordingly, repeated pressing and releasing of the resilient top 22b causes pressurized air to be pumped into the air pillows 18 and 20.

A further tube 28 is coupled to outlet tube 26, and tube 28 extends back into the interior of housing 22a. Tube 28 is attached to a spring-loaded manually operated release valve 30, of any appropriate construction. Release valve 30 is conveniently mounted at the upper end of housing 22a to be readily accessible to the wearer of the knee brace whenever it is desired to deflate the air pillows 18 and 20. At that time, it is merely necessary to depress release valve 30 and cause the compressed air in pillows 18 and 20 to be exhausted to the atmosphere.

The invention provides, therefore, an improved orthopedic knee brace suspension system which includes air pillows on its upper cuff, and which also includes an air pump attached to the knee brace by which the air pillows in the upper cuff are inflated to assure that there is no downward slippage of the upper cuff along the thigh of the wearer. As described above, the pump is constructed and located so that the air pillows may be easily and conveniently deflated when so desired.

While a particular embodiment of the invention has been shown and described, modifications may be made, and it is intended in the following claims to cover all such modifications which fall within the true spirit and scope of the invention.

We claim:

1. In combination: An orthopedic knee brace including an upper cuff having at least one air pillow mounted thereon at the lower end thereof to hold the upper cuff from slipping when the air pillow is inflated; a pump mounted on the outer surface of said upper cuff, said pump comprising: a pump housing having an inlet at the upper end thereof and having an outlet at the lower end thereof, a first tube coupling said outlet to said air pillow, and said pump housing having a resilient top serving as an inflater for said air pillow, first and second one-way valves respectively mounted in the inlet and outlet of said pump housing so that pressure applied to said resilient top causes said first valve to close and forces pressurized fluid through said outlet and through said second valve and through said first tube into the interior of said air pillow, and release of said resilient top causes said second valve to close and causes pressurized fluid to be drawn into the interior of said pump housing through said inlet and through said first valve; a release valve mounted on said cuff adjacent to the upper end of said pump and in a position to be readily accessible to the wearer of said cuff, and a second tube having a lower end coupled to said first tube and having an upper end coupled to said release valve for coupling said first tube to said release valve to enable said release valve to serve as a deflator for said pillow.

2. The pump defined in claim 1, in which said release valve is a spring-loaded manually operated valve.

* * * * *